(12) United States Patent
Upadhyayula et al.

(10) Patent No.: US 11,053,277 B2
(45) Date of Patent: Jul. 6, 2021

(54) PROCESS FOR PREPARATION OF A PEPTIDE

(71) Applicant: INDIAN INSTITUTE OF TECHNOLOGY DELHI, New Delhi (IN)

(72) Inventors: Sreedevi Upadhyayula, New Delhi (IN); Tanmoy Patra, New Delhi (IN); Subhasis Paul, New Delhi (IN)

(*) Notice: Subject to any disclaimer, the term of this patent is extended or adjusted under 35 U.S.C. 154(b) by 0 days.

(21) Appl. No.: 16/474,678

(22) PCT Filed: Dec. 28, 2017

(86) PCT No.: PCT/IN2017/050624
§ 371 (c)(1),
(2) Date: Jun. 28, 2019

(87) PCT Pub. No.: WO2018/122875
PCT Pub. Date: Jul. 5, 2018

(65) Prior Publication Data
US 2020/0123196 A1    Apr. 23, 2020

(30) Foreign Application Priority Data
Dec. 28, 2016  (IN) .............................. 201611044692

(51) Int. Cl.
*C07K 1/04* (2006.01)
(52) U.S. Cl.
CPC .................................... *C07K 1/042* (2013.01)
(58) Field of Classification Search
CPC ........... C07K 1/042; C07K 1/02; C12P 21/06; C07H 21/00; C07H 3/06
See application file for complete search history.

(56) References Cited

U.S. PATENT DOCUMENTS

| 8,691,941 B2 | 4/2014 | Furukawa et al. |
| 2010/0041869 A1 | 2/2010 | Chan et al. |

FOREIGN PATENT DOCUMENTS

JP    2014139149 A    7/2014

OTHER PUBLICATIONS

Fridkin etal, Annu.Rev.Biochem., 1974, 43, 419-443 (Year: 1974).*
International Search Report for PCT/IN2017/050624 dated Apr. 10, 2018.
Miao, Weishi, et al., "Ionic-Liquid-Supported Peptide Synthesis Demonstrated by the Synthesis of Leu5-Enkephalin," The Journal of Organic Chemistry. 70(8):3251-3255 (2005).

* cited by examiner

*Primary Examiner* — Sudhakar Katakam
(74) *Attorney, Agent, or Firm* — Abelman, Frayne & Schwab; Stefan Knirr; Norman D Hanson

(57) ABSTRACT

The present invention relates to a novel process for preparation of peptides having amino acid chain length in the range of 2-40 comprises the steps: i) attaching an end-blocked amino acid with an ionic liquid based solid support in presence of an ionic solvent to obtain an end-terminal blocked amino acid attached ionic liquid; ii) removing end-terminal blocking agent from the end-terminal blocked amino acid attached ionic liquid of step i) followed by work up to obtain an amino acid attached ionic liquid; iii) repeating steps i) through ii) one or more times to obtain a polypeptide attached ionic liquid; and iv) detaching the polypeptide from the polypeptide attached ionic liquid of step iii) to obtain the polypeptide. Said process does not use any auxiliary reagents like dehydrating agent or activating agent. The use of ionic liquids as supports as well as solvents result in the faster kinetics of the process, the separation issues are reduced, and the process has no racemization issues.

12 Claims, 1 Drawing Sheet

PROCESS FOR PREPARATION OF A PEPTIDE

RELATED APPLICATIONS

This application is a national phase of International Application No. PCT/IN2017/050624 filed Dec. 28, 2017 and claims priority from Indian Patent Application No. 201611044692 filed Dec. 28, 2016, both incorporated by reference in their entirety.

FIELD OF THE INVENTION

The present invention relates to a process for preparation of peptides having amino acid chain length in the range of 2-40 using functionalized ionic liquids as supports as well as solvents. Said process uses terminal blocked amino acids as the precursors without using any auxiliary reagents like dehydrating agent or activating agent. The use of ionic liquids as supports as well as solvents for the preparation of peptides result in the faster kinetics of the process, the separation issues are reduced, and the process has no racemization issues. The proper tuning of ionic liquid functionality minimizes the use of auxiliary reagents.

BACKGROUND OF THE INVENTION

Several processes have been reported till date for the manufacture of di, oligo or polypeptides. All these processes use both homogeneous and heterogeneous phase approach using various functional materials in either liquid phase or solid phase reactions. In general, these processes are comprised of mainly three or four different steps involving several separation as well as purification issues. The process can be divided two different section depending on the approach type. In C-terminal approach, first an N-terminal blocked amino acid is attached to the support in presence of auxiliary reagents like dehydrating agent or activating agent. Secondly, the N-terminal blocking functionality is removed using suitable reaction conditions in an organic solvent. Thirdly, another N-terminal amino acid is attached to the chain to increase the chain length further. Addition of other amino acids follow the similar procedure. Finally, the formed peptide chain is detached from the liquid or the solid support and further washed and purified. In the N-terminal approach the same procedure is followed where, the C-terminal blocked amino acid is used instead of the N-terminal blocked amino acids. Due to all these increased number of steps, these processes suffer with separation as well as purification problems. Overall, the yield and purity of the peptides decrease in these type of processes. Several support materials have been reported till date for both homogeneous and heterogeneous phase peptide manufacture process. Heterogeneous support materials provide several advantages over the homogeneous ones in terms of easy purification, automation of the process, etc. Again, heterogeneous supports show conventionally poor kinetics, unequal distribution, retarded coupling, erroneous sequence accumulations, poor loading capability, etc.

US 20060149035 discloses a process involving ionic liquids as solvents for the synthesis and selective biocatalytic modification of peptides, peptide mimetics and proteins. N-terminal biocatalytic modifications were performed at room temperature and a particular pH using peptides containing of 30 to 250 amino acids where ionic liquid was used as a solvent in the process in presence of protease. The ionic liquids were used as solvents only in this process and other potential functionalities of the ionic liquids were not used. Also, the use of peptide hydrolase, peptidases make the process costly from industrial view point.

In addition, EP2107067 discloses a method of synthesizing a dipeptide, an oligopeptide or polypeptide where coupling of an amino acid or peptide to a second amino acid or peptide were conducted in the presence of a boron compound. The boron compound were comprised of a boron oxygen bond, which catalyzed the formation of a peptidic bond. In this method, one of the stereoisomers was found to form in excess of the other stereoisomer or stereoisomers. The racemization of the formed peptide and low overall yield using these boron based supports make this process inefficient.

US20100041869 discloses a set of ionic liquids to be used as a liquid phase support in peptide synthesis comprising of 2 to 30 monomer units. In this method at least one monomer was attached to the ionic liquid based solid support followed by addition of one or more oligopeptides and detachment of the formed peptide from the ionic liquid based solid support. Use of viscous ionic liquids as support material decreases the overall yield in this process.

US008691941 discloses an ionic liquid based solid supported di, oligo or polypeptide synthesis. First, the amino acid was converted into its ionic liquid form and then further amino acids were added to the chain in presence of peptide hydrolases or condensation agents to yield di, oligo or polypeptides. The kinetics of the reaction was slow because of the highly viscous Phosphonium based ionic liquid based solid supports and the overall reaction time for the addition of a single amino acids was as high as 3 days.

A number of research papers have been published till date in this field. In 1963, R. B. Merrifield, *J. Am. Chem. Soc.*, 1963, 85, 2149 disclosed a solid resin like supported material as a support for the manufacture of a tetrapeptide. The resin like supported material resulted in very high overall improved yield without any major separation issues. The use of these support material resulted in several advantages like easy purification of excess reagents by simple filtration and washing, easy separation of the products, parallel library synthesis and automation. Still, this process suffers from poor loading capacity of the resins, retarded kinetics and hence slower reaction, erroneous sequence accumulation, etc.

Visser et al in *Tetrahedron Lett.*, 2003, 44, 9013-9016 discloses a new class of fluorous tagged molecules for the purification of peptides resulting in high purity. The fluorous tagging resulted in high purity but poor yield of the peptides. Mizuno et al in *Chem. Commun.*, 2003, 8, 972-3 disclosed a homogeneous soluble polymeric support materials for the manufacture of di, oligo or polypeptides. Three different type of fluorous supports were reported to be used as support for this process.

Montanari et al in *J. Am. Chem. Soc.*, 2004, 126, 9528-9529 disclosed a new fluorous capping reagent for facile purification of peptides synthesized on the solid phase. Mizuno et al in *Tetrahedron Lett.*, 2004, 45, 3425-3428 disclosed synthesis of new fluorous supports to prepare a peptide having a C-terminal —COOH based on fluorous chemistry. The fluorine containing support was used for the synthesis of a pentapeptide or a peptide derivative. A bioactive peptide, Leu-enkephalin, was easily synthesized using Fmoc-strategy based on fluorous chemistry. This leads to a separation between fluorous phase and organic phase which simplify the separation and purification step. Although it has several advantages over SPPS and ease of purification of products, it shows some limitations such as very low loading capacity, poor automation, and alteration of solubility during synthesis of longer peptide, expensive solvents, etc.

Erbeldinger et al in Biotechnology Progress 2000; 16(6): 1129-1131 disclosed the first use of ionic liquids (4-methyl-N-butyl-pyridinium tetrafluoro borate) for the thermolysin catalyzed synthesis of a peptide Z-aspartame. The ionic liquid was simply used as a substitute solvent for the reaction resulting in improved yield in the process and the enzyme was reported to gain stability in presence of the ionic liquid. Again, the reactions were carried out at very low concentrations. Vallette et al in *Tetrahedron Lett.*, 2004, 45, 1617-1619 disclosed a process using ionic liquid as solvent for the peptide synthesis step. Use of the ionic liquids proved to be advantageous than the conventional organic solvents in terms of the improved yield of the hindered peptide. The ionic liquid was only used as an organic solvent substitute in the process which resulted in straightening of the peptide chain making the formation of the hindered peptides feasible.

Miao et al in *J. Org. Chem.*, 2005, 70, 3251-3255 disclosed an ionic liquid as a support for a pentapeptide synthesis in presence of dehydrating as well as activating agents. One of the major concerns in this type of reactions, the racemization of the amino acids was found to be negligible with the use of these ionic liquids as liquid phase support. The major drawbacks of this process were the retarded kinetics because of the viscous ionic liquid and the use of auxiliary dehydrating and activating agent increasing the separation problems.

Celine Roche et al in *Tetrahedron*, 2010, 66, 8325-8334 disclosed the use of ionic liquids in combination with the onium salt to provide soluble supports for the synthesis of smaller peptides. In spite of several advantages like faster kinetics, high yield and purity of the peptides, easy separation by simple washing and filtration, it has several disadvantages like costly starting material and its complicated preparation procedure, use of dehydrating and activating agent, etc.

From the list of several support materials used in the process, the use of ionic liquids have shown tremendous promises to overcome the present issues in this field. The use of ionic liquids as supports as well as solvents for the manufacture of peptides have several advantages like more control of the process by controlling the solubility and improving the separation issues, faster kinetics, no racemization issues in the reaction, etc. Still, the reported materials are not suitable for the manufacture of few typical peptides containing multiple acidic or basic functionalities where the C-terminal approach is not good enough. Many of the reported ionic liquids were comprising of very high viscosity and hence, resulted in retarded kinetics. The use of auxiliary reagents by properly tuning the ionic liquid functionality can also be minimized.

The use of N-terminal approach and C-terminal approach for the manufacture of peptides containing multiple functionality is not reported in the literature. The combination of an ionic liquid as an active part of the solid support and another ionic liquid as a solvent for the peptide manufacture process to get rid of the excess use of the volatile organic solvents is not reported till date. The removal of the dehydrating agent and the activating agent in the process by incorporating those functionalities in the ionic liquid based solid support itself is not reported till date.

SUMMARY OF THE INVENTION

The present invention provides a process for preparation of a peptide having amino acid chain length in the range of 2-40, said process comprising:

i) attaching first terminal-blocked amino acid with an ionic liquid based solid support in presence of an ionic solvent to obtain a terminal blocked amino acid attached ionic liquid;

ii) removing a terminal blocking group from the terminal blocked amino acid attached ionic liquid to obtain an amino acid attached ionic liquid;

iii) attaching second terminal blocked amino acid and thereafter removing the terminal blocking agent, repeatedly for more than one time to obtain an ionic liquid attached with peptide having amino acid chain length in the range of 2-40; and iv) detaching the peptide having amino acid chain length in the range of 2-40 from the ionic liquid.

An aspect of invention provides a process which uses terminal blocked amino acids as the precursors without using any auxiliary reagents like dehydrating agent or activating agent. The use of ionic liquids as supports as well as solvents for the preparation of peptides result in the faster kinetics of the process, the separation issues are reduced, and the process has no racemization issues. The proper tuning of ionic liquid functionality minimizes the use of auxiliary reagents.

These and other features, aspects, and advantages of the present subject matter will become better understood with reference to the following description. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The above and other features, aspects, and advantages of the subject matter will be better understood with regard to the following description and accompanying drawings where:

DETAILED DESCRIPTION OF THE INVENTION

Figure 1:
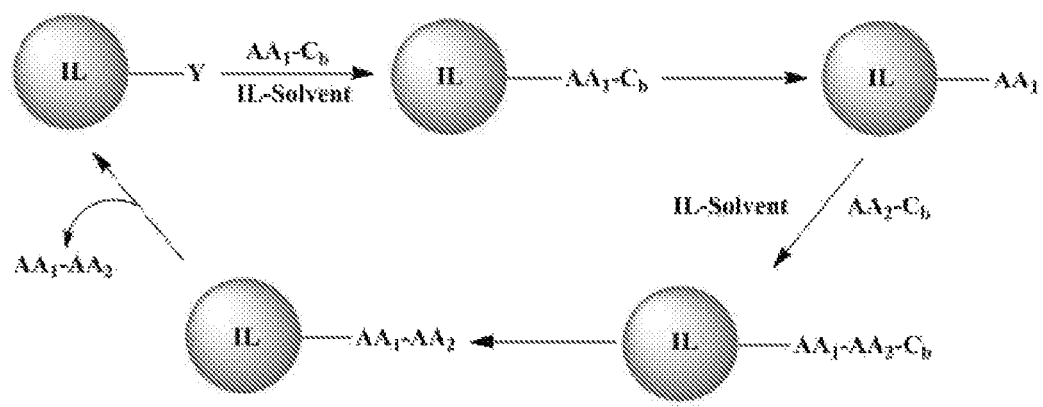
FIG. 1 shows process of preparation of dipeptide via N-terminal approach

The present invention relates to a process for preparation of a peptide having amino acid chain length in the range of 2-40 in an ionic solvent without using any auxiliary reagents like dehydrating agent or activating agent.

In one embodiment of the invention, there is provided a process for preparation of a peptide having amino acid chain length in the range of 2-40, said process comprising:

i) attaching first terminal-blocked amino acid with an ionic liquid based solid support in presence of an ionic solvent to obtain a terminal blocked amino acid attached ionic liquid;

ii) removing the terminal blocking group from the terminal blocked amino acid attached ionic liquid to obtain an amino acid attached ionic liquid;

iii) attaching second terminal blocked amino acid and thereafter removing the terminal blocking agent, repeatedly for more than one time to obtain an ionic liquid attached with peptide having amino acid chain length in the range of 2-40; and iv) detaching the peptide having amino acid chain length in the range of 2-40 from the ionic liquid.

In one embodiment of the invention, the first and the second terminal blocked amino acids can be same or different.

In another embodiment of the invention, the attaching first N- or C-terminal-blocked amino acid with the ionic liquid based solid support is carried out by contacting the ionic liquid based solid support with the terminal blocked amino acid for a time period in the range of 2 to 4 hours.

In another embodiment of the invention, the attachment of the first N- or C-terminal-blocked amino acid with the ionic liquid based solid support is carried out at a temperature in the range of 27° C. to 60° C.

In another embodiment of the invention, the ionic solvent is selected from the group consisting of a cationic part with a heteroatom containing component selected from a group of triethylamine, diethanolamine, triethanolamine, diethyl amine, imidazole, triethylphosphine and combinations thereof; a halogen containing polymeric solid support selected from a group of chloromethyl polystyrene, hydroxyethylpolystyrene, divinyl benzene crosslinked chloromethyl polystyrene and combinations thereof; a hydrophobic or less hydrophilic anion selected from a group of tetrafluoroborate, bistrifluoromethane sulfanimide, trifluoromethane sulfonate, hexafluorophosphate and combinations thereof; a side alkyl chain containing at least 2 to 8 carbon atoms, preferably 2 to 6 carbon atoms, more preferably 2 to 4 carbon atoms; a blocking functionality at the end of the side chain selected from a group of —COOH, —COCl, —SOCl, —COOEt, —COOMe and combinations thereof.

In another embodiment of the invention, the ionic liquid based solid support comprises of a heteroatom containing cationic functionality selected from a group consisting of imidazole, diethanolamine, triethylamine, triethanolamine, diethyl amine, pyridine and triethylphosphine and combinations thereof; a side chain containing —$CH_2$ groups in between 2 to 8, preferably 2 to 6, more preferably 2 to 4 and combinations thereof; a side chain end group functionality selected from a group of —Cl, —Br, —OH, —I and combinations thereof.

In another embodiment of invention, the terminal blocking group is selected from a group consisting of ester, ether, carbamate, and acid chloride linkage.

In another embodiment of the invention, the process has a water content less than 5% by volume.

In another embodiment of the invention, the terminal-blocked amino acid is a C-terminal blocked amino acid.

In another embodiment of invention, the terminal-blocked amino acid is an N-terminal blocked amino acid.

In another embodiment of the invention, the peptide is detached from the ionic liquid by reacting with a base selected from a group consisting of sodium hydroxide, potassium hydroxide, and lithium hydroxide or combinations thereof for a time period in the range of 30 mins to 2 hours in a solvent selected from a group consisting of tetrahydrofuran, water, and ethanol or combinations thereof.

In another embodiment of the invention, the peptide is detached from the ionic liquid by reacting with an acid selected from a group consisting of trifluoroacetic acid, acetic acid, and trifluromethane sulfonic acid or combinations thereof for a time period in the range of 30 mins to 2 hour in a solvent selected from a group consisting of tetrahydrofuran, water, dichloromethane and ethanol or combinations thereof.

The present invention is further described in terms of N-terminal peptide synthesis approach and C-terminal peptide synthesis approach.

When end-blocked amino acid is C-terminal blocked amino acid, N-terminal peptide synthesis approach is used for preparation of a polypeptide which is as shown in FIG. 1. Referring to FIG. 1, the terms "$AA_1$-$C_b$" and "$AA_2$-$C_b$" represent C-terminal blocked amino acids, the term "IL-Solvent" represents ionic liquid as solvent, the term "IL-Y" represents ionic liquid based support. The C-terminal blocked amino acid $AA_1$-$C_b$ is attached to the ionic liquid based solid support (IL-Z) in presence of the same or different ionic liquid as a solvent to obtain C-terminal blocked amino acid attached to ionic liquid. After addition of each C-terminal blocked amino acid, the C-terminal blocking functionality was removed under mild reaction conditions. Finally, the formed peptide was detached from the ionic liquid based solid support and the yield as well as purity of the peptide was checked using $^1$H NMR and HPLC analysis.

Figure 2:
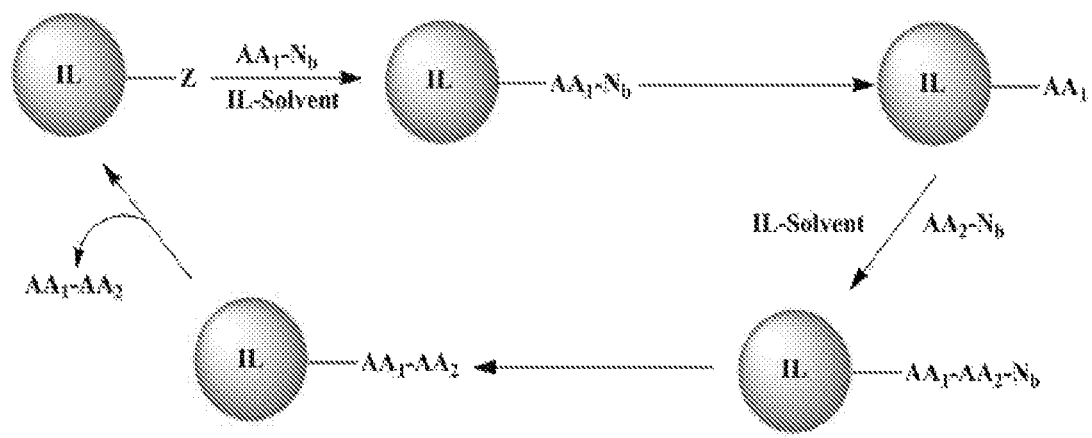
FIG. 2 shows process of preparation of dipeptide via C-terminal approach

When end-blocked amino acid is N-terminal blocked amino acid, C-terminal peptide synthesis approach is used for preparation of a polypeptide which is as shown in FIG. 2. Referring to FIG. 2, the terms "$AA_1$-$N_b$" and "$AA_2$-$N_b$" represent C-terminal blocked amino acids, the term "IL-Solvent" represents ionic liquid as solvent, the term "IL-Z" represents ionic liquid based support. The N-terminal blocked amino acid $AA_1$-$N_b$ is attached to the ionic liquid based solid support (IL-Z) in presence of the same or different ionic liquid as a solvent to obtain N-terminal blocked amino acid attached to ionic liquid. After addition of each N-terminal blocked amino acid, the N-terminal blocking functionality was removed under mild reaction conditions. Finally, the formed peptide was detached from the ionic liquid based solid support and the yield as well as purity of the peptide was checked using $^1$H NMR and HPLC analysis.

In an embodiment of the invention for N-terminal approach, ionic liquid based support material is used along with an ionic liquid solvent in combination for preparation of peptides having amino acid chain length in the range of 2-40. Said ionic liquid based solid support comprise of a cationic functionality selected from a group consisting of imidazole, diethanolamine, triethylamine, triethanolamine, diethyl amine, pyridine and triethylphosphine, and combinations thereof; a side chain containing —$CH_2$ groups in between 2 to 8, preferably 2 to 6, more preferably 2 to 4 and combinations thereof; a side chain end group functionality selected from a group of —COOH, —COCl, —SOCl, —COOEt, —COOMe and combinations thereof; an anionic species selected from a group of methane sulfonate, triflate, hexafluorophosphate, trifluoromethanesulfonate, tetrafluroborate, and combinations thereof. The heteroatom containing functionality was reacted with the side chain containing functionality in an organic solvent selected from a group of toluene, acetonitrile, ethanol, acetone and combinations thereof at temperature in the range of 40° C. to 110° C., preferably in the range of 60° C. to 110° C. The resultant solid or the liquid product was further washed using common organic solvents like diethyl ether, acetone, ethanol, toluene and combinations thereof. The anion metathesis was carried out using an anionic source containing species in a solvent selected from a group of dichloromethane, water, ethanol and combinations thereof. Finally, the ionic liquid was reacted with the polymeric solid support selected from a group of chloromethyl polystyrene, hydroxyethyl polystyrene, divinyl benzene cross-linked chloromethyl polystyrene and combinations thereof under mild reaction conditions to obtain ionic liquid based solid support.

In an embodiment of the invention for C-terminal approach, ionic liquid based support material is used along with an ionic liquid solvent in combination for preparation of peptides having amino acid chain length in the range of 2-40. Said ionic liquid based solid support comprise of a heteroatom containing cationic functionality selected from a group consisting of imidazole, diethanolamine, triethylamine, triethanolamine, diethyl amine, pyridine and triethylphosphine and combinations thereof; a side chain containing —$CH_2$ groups in between 2 to 8, preferably 2 to 6, more preferably 2 to 4 and combinations thereof; a side chain end group functionality selected from a group of —Cl, —Br, —OH, —I and combinations thereof; an anionic species selected from a group of methane sulfonate, triflate, hexafluorophosphate, trifluoromethanesulfonate, tetrafluroborate and combinations thereof. The heteroatom containing functionality was reacted with the side chain containing functionality in an organic solvent selected from a group of toluene, acetonitrile, ethanol, acetone and combinations thereof at temperature in the range of 40° C. to 110° C., preferably in the range of 60° C. to 110° C., the resultant solid or the liquid product was further washed using common organic solvents like diethyl ether, acetone, ethanol, toluene and combinations thereof. The anion metathesis was carried out using an anionic source containing species in a solvent selected from a group of dichloromethane, water, ethanol and combinations thereof. Finally, the ionic liquid was reacted with the polymeric solid support selected from a group of chloromethyl polystyrene, hydroxyethyl polystyrene, divinyl benzene cross-linked chloromethyl polystyrene and combinations thereof under mild reaction conditions to obtain ionic liquid based solid support.

In another embodiment of the invention, the ionic liquid solvent used is same as that used in the solid support. In another aspect of the invention, the ionic liquid solvent used is different as that used in the solid support such that the internal electrostatic interaction does not affect the overall outcome of the process. In another embodiment of the invention, the ionic solvent is selected from the group triethylamine, diethanolamine, triethanolamine, diethyl amine, imidazole, triethylphosphine based functionalized ionic liquid.

In an embodiment of the invention, there is provided a process for the manufacture of peptides having amino acid chain length in the range of 2-40 via N-terminal approach, wherein the support material is contacted with a C-terminal blocked amino acid, reacted for 30 min to 1 h, and the blocking functionality was removed thereafter under mild reaction conditions.

In an embodiment of the invention, there is provided a process for the manufacture of peptides having amino acid chain length in the range of 2-40 via C-terminal approach, wherein the support material is contacted with an N-terminal blocked amino acid, reacted for 10 min to 1 h, and the blocking functionality was removed thereafter under mild reaction conditions.

In an embodiment of the invention, the attaching of the terminal-blocked amino acid with the ionic liquid based solid support is carried out at a temperature in the range of 27° C. to 60° C.

In an embodiment of the present disclosure, there is provided a process for the manufacture of peptides having amino acid chain length in the range of 2-40 via N-terminal approach, wherein the formed peptide was detached from the ionic liquid based solid support by reacting with a base selected from a group of Sodium, hydroxide, Potassium hydroxide, Lithium hydroxide and combinations thereof for 30 mins to 2 h in a solvent selected from a group of tetrahydrofuran, water, ethanol and combinations thereof.

In an embodiment of the present disclosure, there is provided a process for the manufacture of peptides having amino acid chain length in the range of 2-40 via C-terminal approach, wherein the formed peptide was detached from the ionic liquid based solid support by reacting with an acid selected from a group of trifluoroacetic acid, acetic acid, trifluromethane sulfonic acid and combinations thereof for 30 mins to 2 h in a solvent selected from a group of tetrahydrofuran, water, ethanol and combinations thereof.

In an embodiment of the present disclosure, there is provided a process for the manufacture of peptides having amino acid chain length in the range of 2-40, wherein an ionic liquid based solid support material was used in combination with an ionic liquid solvent to obtain high yield of the peptides with very high purity.

In an embodiment of the present disclosure, there is provided a process for the manufacture of peptides having amino acid chain length in the range of 2-40, wherein a functionalized ionic liquid based solid support material in combination with the same or another ionic liquid used as a solvent for the reaction.

In an embodiment of the present disclosure, there is provided a process for the manufacture of peptides having amino acid chain length in the range of 2-40, wherein the end group of the ionic liquid based solid support material is designed to block the C-terminal or the N-terminal of the amino acids to be attached. The first step of this process start by attaching the one end (either N- or C-) blocked amino acid from either the C-terminal end or the N-terminal end under mild reaction conditions.

In an embodiment of the present disclosure, there is provided a process for the manufacture of peptides having amino acid chain length in the range of 2-40, wherein the used amino acids were blocked from either the N-terminal or the C-terminal end. The blocking functionalities of the amino acids are removed after addition of each amino acids using the conventional methods under mild reaction conditions.

In an embodiment of the present disclosure, there is provided a process for the manufacture of peptides having amino acid chain length in the range of 2-40, wherein the water content of the reaction system can be reduced by connecting to a vacuum line maintain a pressure of less than 50 mm of Hg, preferably less than 30 mm of Hg, more preferably less than 10 mm of Hg.

In an embodiment of the present disclosure, there is provided a process for the manufacture of peptides having amino acid chain length in the range of 2-40, wherein the used C-terminal or N-terminal blocked amino acid components were selected from a group of Leucine, Glycine, Aspartic acid, lysine, Tryptophan, Phenyl alanine, and combinations thereof.

Removal of any moisture from the ionic liquid based solid support is an essential part of the process. After the detachment of the ionic liquid from the formed peptide to regenerate the support as well as the solvent ionic liquid is to be performed by washing both the component with organic solvents like dichloromethane, acetonitrile, toluene, diethyl ether thrice with a volume of around 3 times the feed used. After washing the ionic liquid components must be dried at 120° C. under reduced pressure of around 10 mm of Hg for around 5 to 8 h. In an aspect of the present disclosure, there is provided a process for the manufacture of peptides having amino acid chain length in the range of 2-40, wherein the water content of the reaction system is in between of 1-40%, preferably in between 1-20%, more preferably in between 1-5% by volume.

In an embodiment of the present disclosure, there is provided a process for the manufacture of peptides having amino acid chain length in the range of 2-40, wherein the reaction system is free from any peptide hydrolase and/or coupling or dehydrating agent. The reaction system is free from any peptide hydrolase and/or coupling agent and/or dehydrating agent means it contains less than 1 molar equivalent, preferably less than 0.1 molar equivalent, more preferably less than 0.01 molar equivalent of these components with respect to the amino acids used.

The HPLC analysis was conducted under normal procedures, but preferably under conditions stated hereinafter. The products were analyzed using Agilent Hi-Plex H column (300×7.7 mm), flow rate of 2.0 mL/min; a stop time of 40 min; detection wavelength of 210 nm; a 200:1 ratio mixture of (100 mM of $NaH_2PO_4$+5 mM of sodium 1-octanesulfonate) to acetonitrile; injection volume 10 μL. Alternatively, flow rate of 2.0 mL/min; a stop time of 40 min; detection wavelength of 210 nm; a 90:10 ratio mixture of (100 mM of $NaH_2PO_4$+5 mM of sodium 1-octanesulfonate) to acetonitrile; injection volume 01 μL. Alternatively, flow rate of 2.0 mL/min; a stop time of 40 min; detection wavelength of 210 nm; a 5:1 ratio mixture of (50 mM of $NaH_2PO_4$+5 mM of sodium 1-octanesulfonate) to methanol; injection volume 10 μL The present invention is more particularly described in the following examples, that are intended as illustrations only, since numerous modifications and variations within the scope of the present invention will be apparent to those skilled in the art. Unless otherwise noted, all parts, percentages and ratios reported in the following examples are on a weight basis and all reagents used in the examples were obtained or are available from the chemical suppliers.

EXAMPLES

Example 1

Attachment of Amino Acid to the Ionic Liquid Based Solid Support via N-Terminal Approach The reaction mixture containing L-Phenyl alanine methyl ester and ionic liquid based solid support IL-Y at 1.1:1 mole ratio was charged in a peptide vessel glass reactor in the ionic liquid solvent IL-Solvent under stirring condition with nitrogen flow and/or shaking at room temperature for 2 to 4 h at a temperature of 37° C. At the end of the reaction, the solvent along with excess amino acid was first separated from the solid mass and then separated from the amino acids by extraction using dichloromethane. The ester linkage was deprotected by treating with trifluoroacetic acid and then with triethylamine. Similarly, other C-terminal blocked Glycinyl methyl ester was attached to the chain under stirring condition with nitrogen flow and/or shaking at room temperature for 2 to 4 h at a temperature of 37° C. and the ester part was removed to obtain a dipeptide, Phe-Gly, attached to the ionic liquid based solid support.

Example 2

Detachment of the Peptide from the Ionic Liquid Based Solid Support via N-Terminal Approach The formed dipeptide, Phe-Gly was detached from the ionic liquid based solid support by treating with small amount of NaOH in THF and water mixture (2:1) for 30 min to 4 h under stirring and/or shaking conditions inside the glass reactor, followed by acidification at pH 5.0. The dipeptide was separated after washing and then qualitatively as well as quantitatively analyzed using a $^1H$ NMR and HPLC analysis respectively.

Example 3

Manufacture of a Pentapeptide Using Ionic Liquid Based Solid Support via N-Terminal Approach The reaction mixture containing L-Tyrosine methyl ester hydrochloride and ionic liquid based solid support IL-Y at 1.1:1 mole ratio was charged in a peptide vessel glass reactor in the ionic liquid solvent IL-Solvent under stirring condition with nitrogen flow and/or shaking for 2 to 4 h at a temperature of 37° C. At the end of the reaction, the solvent along with excess amino acid was first separated from the solid mass and then separated from the amino acids by extraction using dichloromethane. The ester linkage was deprotected by treating with trifluoroacetic acid and then with triethylamine. Similarly, stepwise C-terminal blocked amino acids sequentially, two times glycine methyl ester, L-Phenylalanine methyl ester hydrochloride and L-Leucine methyl ester hydrochloride were attached to the chain under stirring condition with nitrogen flow and/or shaking for 2 to 4 h at a temperature of 37° C. and the ester part was removed subsequently in each step to obtain a pentapeptide, Tyr-Gly-Gly-Phe-Leu, attached to the ionic liquid based solid support. The formed pentapeptide, Tyr-Gly-Gly-Phe-Leu was detached from the ionic liquid based solid support by treating with small amount of NaOH in THF and water mixture (2:1) for 30 min to 4 h under stirring and/or shaking conditions inside the glass reactor, followed by acidification at pH 5.0. The pentapeptide was separated after washing and then qualitatively as well as quantitatively analyzed using a $^1H$ NMR and HPLC analysis respectively.

Example 4

Manufacture of a Polypeptide Using Ionic Liquid Based Solid Support via N-Terminal Approach The reaction mixture containing L-Tyrosine methyl ester hydrochloride and ionic liquid based solid support IL-Y at 1.1:1 mole ratio was charged in a peptide vessel glass reactor in the ionic liquid solvent, IL-Solvent, under stirring condition with nitrogen flow and/or shaking for 2 to 4 h at a temperature of 37° C. At the end of the reaction, the solvent along with excess amino acid was first separated from the solid mass and then separated from the amino acids by extraction using dichloromethane. The ester linkage was deprotected by treating with trifluoroacetic acid and then with triethylamine. Similarly, stepwise C-terminal blocked amino acids, two times glycine methyl ester, L-Phenylalanine methyl ester hydrochloride and L-Leucine methyl ester hydrochloride were attached sequentially to the chain under stirring condition with nitrogen flow and/or shaking for 2 to 4 h at a temperature of 37° C. and the ester part was removed subsequently in each step to obtain a pentapeptide, Tyr-Gly-Gly-Phe-Leu, attached to the ionic liquid based solid support. Further, the same C-terminal blocked amino acid sequence was attached to the chain three more times to form the 20-mer peptide under the same reaction conditions. The formed 20-mer peptide, Tyr-Gly-Gly-Phe-Leu-Tyr-Gly-Gly-Phe-Leu-Tyr-Gly-Gly-Phe-Leu-Tyr-Gly-Gly-Phe-Leu, was detached from the ionic liquid based solid support by treating with small amount of NaOH in THF and water mixture (2:1) for 30 min to 4 h under stirring and/or shaking conditions inside the glass reactor, followed by acidification at pH 5.0. The 20-mer peptide was separated after washing and then qualitatively as well as quantitatively analyzed using a $^1$H NMR and HPLC analysis respectively.

Example 5

Effect of Temperature via N-Terminal Approach

The temperature of the reactor in the process mentioned in Example 1 was varied in the range of 27° C. to 50° C. for the attachment of the ionic liquid to the ionic liquid based solid support. The reaction was finished within 24 h after the initiation of the mixture with proper mixing by stirring the components and/or shaking the reactor. Variation in the overall yield of the peptides as a result of the variation in temperature are summarized in Table 1 below:

TABLE 1

Effect of temperature via N-terminal approach

| Peptide | Yield of Peptide at various temperatures (%) | | |
|---|---|---|---|
| | 27° C. | 37° C. | 50° C. |
| Phe-Phe | 96.2 | 97.5 | 98.6 |
| Phe-Gly | 98.4 | 99.6 | 99.9 |
| Phe-Lys | 92.5 | 93.8 | 95.1 |
| Phe-Asp | 93.9 | 95.2 | 96.6 |
| Phe-Gly-Asp-Lys | 92.1 | 94.1 | 95.2 |
| Tyr-Gly-Gly-Phe-Leu | 91.9 | 92.8 | 94.3 |
| 20-mer peptide | 58.2 | 61.6 | 63.4 |

Example 6

Attachment of Amino Acid to the Ionic Liquid Based Solid Support via C-Terminal Approach The reaction mixture containing Boc-Leu and ionic liquid based solid support IL-Z at 1.1:1 mole ratio was charged in a peptide vessel glass reactor in the ionic liquid solvent IL-Solvent under stirring condition with nitrogen flow and/or shaking for 2 to 4 h at a temperature of 37° C. At the end of the reaction, the solvent along with excess amino acid was first separated from the solid mass and then separated from the amino acids by extraction using dichloromethane. The Boc linkage was deprotected by treating with small amount of NaOH in THF and water mixture (2:1) in the glass reactor under stirring and/or shaking for about 30 min to 4 h, followed by acidification at pH 5.0. Similarly, other C-terminal blocked Fmoc-Gly was attached to the chain under stirring condition with nitrogen flow and/or shaking at room temperature for 2 to 4 h at a temperature of 37° C. and the Fmoc part was removed by treating with piperidine in dichloromethane solvent under stirring and/or shaking inside the reactor for 5 min to 2 h to obtain a dipeptide, Leu-Gly, attached to the ionic liquid based solid support.

Example 7

Detachment of the Peptide from the Ionic Liquid Based Solid Support via C-Terminal Approach The formed dipeptide, Leu-Gly was detached from the ionic liquid based solid support by treating with small amount of trifluoroacetic acid followed by triethylamine for 30 min to 4 h under stirring and/or shaking conditions inside the glass reactor. The obtained dipeptide was separated after washing and then qualitatively as well as quantitatively analyzed using a $^1$H NMR and HPLC analysis.

Example 9

Manufacture of a Pentapeptide Using Ionic Liquid Based Solid Support via C-Terminal Approach The reaction mixture containing Boc-Leu and ionic liquid based solid support IL-Z at 1.1:1 mole ratio was charged in a peptide vessel glass reactor in the ionic liquid solvent IL-Solvent under stirring condition with nitrogen flow and/or shaking for 2 to 4 h at a temperature of 37° C. At the end of the reaction, the solvent along with excess amino acid was first separated from the solid mass and then separated from the amino acids by extraction using dichloromethane. The Boc linkage was deprotected by treating with small amount of NaOH in THF and water mixture (2:1) in the glass reactor under stirring and/or shaking for about 30 min to 4 h, followed by acidification at pH 5.0. Similarly, other N-terminal blocked amino acids sequentially, Fmoc-L-Phe-OH, two times Fmoc-Gly-OH and Fmoc-L-Tyr(tBu)-OH were attached to the chain under stirring condition with nitrogen flow and/or shaking for 2 to 4 h at a temperature of 37° C. and the Fmoc part was removed in each step subsequently by treating with piperidine in dichloromethane solvent under stirring and/or shaking inside the reactor for 5 min to 2 h to obtain a pentapeptide, Tyr-Gly-Gly-Phe-Leu, attached to the ionic liquid based solid support. Further, the same N-terminal blocked amino acid sequence was attached to the chain three more times to form the 20-mer peptide under the same reaction conditions. The formed 20-mer peptide, Tyr-Gly-Gly-Phe-Leu-Tyr-Gly-Gly-Phe-Leu-Tyr-Gly-Gly-Phe-Leu-Tyr-Gly-Gly-Phe-Leu, was detached from the ionic liquid based solid support by treating with small amount of trifluoroacetic acid followed by triethylamine for 30 min to 4 h under stirring and/or shaking conditions inside the glass reactor. The obtained pentapeptide was separated after washing and then qualitatively as well as quantitatively analyzed using a $^1$H NMR and HPLC analysis.

Example 10

Manufacture of a Polypeptide Using Ionic Liquid Based Solid Support via C-Terminal Approach The reaction mixture containing Boc-Leu and ionic liquid based solid support IL-Z at 1.1:1 mole ratio was charged in a peptide vessel glass reactor in the ionic liquid solvent IL-Solvent under stirring condition with nitrogen flow and/or shaking for 2 to 4 h at a temperature of 37° C. At the end of the reaction, the solvent along with excess amino acid was first separated from the solid mass and then separated from the amino acids by extraction using dichloromethane. The Boc linkage was deprotected by treating with small amount of NaOH in THF and water mixture (2:1) in the glass reactor under stirring and/or shaking for about 30 min to 4 h, followed by acidification at pH 5.0. Similarly, other N-terminal blocked amino acids sequentially, Fmoc-L-Phe-OH, two times Fmoc-Gly-OH and Fmoc-L-Tyr(tBu)-OH were attached to the chain under stirring condition with nitrogen flow and/or shaking for 2 to 4 h at a temperature of 37° C. and the Fmoc part was removed in each step subsequently by treating with piperidine in dichloromethane solvent under stirring and/or shaking inside the reactor for 5 min to 2 h to obtain a pentapeptide, Tyr-Gly-Gly-Phe-Leu, attached to the ionic liquid based solid support. The formed pentapeptide, Tyr-Gly-Gly-Phe-Leu, was detached from the ionic liquid based solid support by treating with small amount of trifluoroacetic acid followed by triethylamine for 30 min to 4 h under stirring and/or shaking conditions inside the glass reactor. The obtained pentapeptide was separated after washing and then qualitatively as well as quantitatively analyzed using a ¹H NMR and HPLC analysis.

Example 11

Effect of Temperature via C-Terminal Approach

The temperature of the reactor in the process mentioned in Example 4 was varied in the range of 27° C. to 50° C. for the attachment of the ionic liquid to the ionic liquid based solid support. The reaction was finished within 24 h after the initiation of the mixture with proper mixing by stirring the components and/or shaking the reactor. Variations in the overall yield of the peptides as a result of the variation in temperature are summarized in Table 2 below:

TABLE 2

Effect of temperature via C-terminal approach

| Peptide | Yield of Peptide at various temperatures (%) | | |
|---|---|---|---|
| | 27° C. | 37° C. | 50° C. |
| Leu-Leu | 98.2 | 99.5 | 99.6 |
| Leu-Gly | 98.3 | 98.9 | 99.1 |
| Leu-Lys | 97.6 | 98.2 | 98.9 |
| Leu-Asp | 95.5 | 96.9 | 98.1 |
| Leu-Gly-Asp-Lys | 93.5 | 94.5 | 95.2 |
| Tyr-Gly-Gly-Phe-Leu | 92.8 | 94.1 | 95.0 |
| 20-mer peptide | 64.5 | 66.7 | 68.4 |

The process of preparation of polypeptides for present invention is not limited to the embodiments discussed herein and can be embodied by various modifications within the scope of the following claims. It should be recognized that the preferred embodiments described above are exemplary only. Certain modifications and improvements will occur to the person skilled in the art upon a reading of forgoing description. It should be understood that all such modifications and improvements have been deleted herein for the sake of conciseness and readability but are properly within the scope of the following claims.

We claim:

1. A process for preparation of a peptide having an amino acid chain length of from 2-40 amino acids, said process comprising:
   i) attaching a first terminal-blocked amino acid to an ionic liquid based solid support in the presence of an ionic solvent to obtain a terminal blocked amino acid attached ionic liquid;
   ii) removing a terminal blocking group from the terminal blocked amino acid attached ionic liquid to obtain an amino acid attached ionic liquid;
   iii) attaching a second terminal blocked amino acid to the amino acid attached ionic liquid and thereafter removing the terminal blocking group, repeatedly, to obtain an ionic liquid attached with a peptide having an amino acid chain length of from 2 to 40 amino acids; and
   iv) detaching said peptide from the ionic liquid based solid support, wherein the C-terminal blocked amino acid and wherein the N-terminal blocked amino acid have multiple functionality selected from cationic functionality and ionic liquid functionality
   wherein the ionic liquid based solid support comprises
      a) a heteroatom containing a cationic functionality selected from the group consisting of diethanolamine, triethylamine, triethanolamine, diethyl amine and triethylphosphine and combinations thereof; b) a side chain containing from 2-8 —CH₂ groups and combinations thereof; c) a side chain end group functionality selected from the group consisting of —Cl, —Br, —OH, —I and combinations thereof;
   wherein the preparation of a peptide is N-terminal or C-terminal peptide synthesis approach; wherein the process is free of dehydrating, activating agents and peptide hydrolase.

2. The process as claimed in claim 1, comprising attaching the first terminal-blocked amino acid to the ionic liquid based solid support by contacting the ionic liquid based solid support with the terminal blocked amino acid for a time period of from 2 to 4 hours.

3. The process as claimed in claim 1, comprising attaching the first terminal-blocked amino acid with the ionic liquid based solid support at a temperature of from 27° C. to 60° C.

4. The process as claimed in claim 1, wherein said ionic solvent is triethylamine, diethanolamine, triethanolamine, diethyl amine, imidazole, or a triethylphosphine based functionalized ionic liquid.

5. The process as claimed in claim 1, wherein the terminal blocking group is selected from the group consisting of an ester, an ether, a carbamate, and an acid chloride linkage.

6. The process as claimed in claim 1, wherein the process has a water content is from 1 to 40%.

7. The process as claimed in claim 1, wherein the preparation is N-terminal approach, comprising detaching the peptide from the ionic liquid by reacting said peptide with a base selected from the group consisting of sodium hydroxide, potassium hydroxide, and lithium hydroxide and combinations thereof for from 30 mins to 2 hours in a solvent selected from the group consisting of tetrahydrofuran, water, and ethanol and combinations thereof.

8. The process as claimed in claim 1, wherein the preparation is C-terminal approach, comprising detaching the peptide from the ionic liquid by reacting said peptide with an acid selected from the group consisting of trifluoroacetic acid, acetic acid, and trifluromethane sulfonic acid and combinations thereof for from 30 mins to 2 hour in a solvent selected from the group consisting of tetrahydrofuran, water, and ethanol and combinations thereof.

9. The process of claim 1, wherein said side chain contains from 2 to 6 —CH₂ groups.

10. The process of claim 9, wherein said side chain contains from 2-4 —CH₂ groups.

11. The process of claim 6, wherein the water content is from 1-20%.

12. The process of claim 11, wherein the water content is from 1 to 5%.

* * * * *